(12) United States Patent
Jung et al.

(10) Patent No.: US 11,331,397 B2
(45) Date of Patent: May 17, 2022

(54) LIGHT EMITTING DEVICE

(71) Applicant: SEOUL VIOSYS CO., LTD., Gyeonggi-do (KR)

(72) Inventors: Sang Wook Jung, Gyeonggi-do (KR); Hee Ho Bae, Gyeonggi-do (KR)

(73) Assignee: SEOUL VIOSYS CO., LTD., Gyeonggi-do (KR)

( * ) Notice: Subject to any disclaimer, the term of this patent is extended or adjusted under 35 U.S.C. 154(b) by 22 days.

(21) Appl. No.: 16/707,257

(22) Filed: Dec. 9, 2019

(65) Prior Publication Data

US 2020/0108160 A1 Apr. 9, 2020

Related U.S. Application Data

(63) Continuation of application No. PCT/KR2018/006505, filed on Jun. 8, 2018.

(30) Foreign Application Priority Data

Jun. 9, 2017 (KR) .......................... 10-2017-0072648

(51) Int. Cl.
*A61L 2/00* (2006.01)
*A61L 2/26* (2006.01)
*A61N 5/06* (2006.01)

(52) U.S. Cl.
CPC .............. *A61L 2/0047* (2013.01); *A61L 2/26* (2013.01); *A61N 5/0616* (2013.01); *A61N 5/0624* (2013.01); *A61L 2202/11* (2013.01); *A61N 2005/0645* (2013.01); *A61N 2005/0661* (2013.01)

(58) Field of Classification Search
CPC ...... A61L 2/0047; A61L 2/26; A61L 2202/11; A61N 5/0616; A61N 5/0624
See application file for complete search history.

(56) References Cited

U.S. PATENT DOCUMENTS

2010/0284168 A1* 11/2010 Walter ...................... A61L 9/03
362/96

FOREIGN PATENT DOCUMENTS

| CN | 101674863 A | 3/2010 |
|----|----|----|
| CN | 201833218 | 5/2011 |
| CN | 202191272 U | 4/2012 |
| CN | 103037938 A | 4/2013 |
| KR | 1020130054946 A | 5/2013 |
| KR | 1020130111808 A | 10/2013 |
| KR | 1020150025510 | 3/2015 |
| KR | 1020150025510 A | 3/2015 |

(Continued)

OTHER PUBLICATIONS

Office Action issued in Chinese counterpart Application No. 201880009317.8 dated Mar. 10, 2021, with an English translation thereof.

(Continued)

*Primary Examiner* — Sean E Conley
(74) *Attorney, Agent, or Firm* — Burris Law, PLLC

(57) ABSTRACT

The present disclosure relates to a light emitting device. The light emitting device includes: a device housing having a structure with an open bottom; and a sterilization module installed in the device housing and emitting ultraviolet light for sterilization. Here, the sterilization module emits the ultraviolet light for sterilization to the open bottom of the device housing.

19 Claims, 13 Drawing Sheets

(56) References Cited

FOREIGN PATENT DOCUMENTS

| KR | 1020150135618 | 12/2015 |
| KR | 1020150135618 A | 12/2015 |
| KR | 1020160107036 | 9/2016 |
| KR | 1020160107036 A | 9/2016 |
| TW | M394144 U | 12/2010 |

OTHER PUBLICATIONS

International Search Report and for PCT/KR2018/006505, dated Oct. 17, 2018, 2 pages.
English translation of the Office Action issued in Chinese counterpad Application No. 201880009317.8, dated Sep. 17, 2021, 11 pages.

* cited by examiner

LIGHT EMITTING DEVICE

CROSS-REFERENCE TO RELATED APPLICATION

The present application is a continuation of PCT Application No. PCT/KR2018/006505 filed Jun. 8, 2018 which claims priority to Korean Patent Application No. 10-2017-0072648 filed Jun. 9, 2017 and entitled "Light Emitting Device," the disclosures of which are hereby incorporated in its entirety by reference as set forth herein.

TECHNICAL FIELD

Embodiments of the present disclosure relate to a light emitting device.

BACKGROUND ART

Skin infections caused by bacteria resistant to antibiotics, such as MRSA (Methicillin-resistant *Staphylococcus aureus*) and VRE (Vancomycin Resistant *Enterococcus*), are becoming major issues. In addition, skin infections caused by bacteria frequently occur after surgery or in diabetic patients. Infections caused not only by bacteria resistant to antibiotics but also by other bacteria are fatal to patients with low immunity or to the old and weak.

Skin infections caused by bacteria are generally cured with antibiotics. However, skin infections caused by bacteria resistant to the antibiotics can be cured only with a limited kind of antibiotics. Moreover, treatment of the skin infections with the antibiotics requires a long period of time and entails side effects, high costs and stress on the patients.

Therefore, there is a need for various and different curing methods in addition to treatment of skin disease caused by bacterial infection using antibiotics.

SUMMARY

Embodiments of the present disclosure provide a light emitting device capable of curing skin infected with bacteria. Embodiments of the present disclosure provide a light emitting device for skin care, which is easy to carry and can be used even during users' activity. Embodiments of the present disclosure provide a light emitting device capable of curing not only bacterial infections but also various diseases.

According to one embodiment of the present disclosure, a light emitting device includes a device housing open at a lower portion thereof; and a sterilization module disposed in the device housing and emitting UV light for sterilization. The sterilization module emits UV light for sterilization toward the open lower portion of the device housing.

According to embodiments of the present disclosure, the light emitting device can cure the skin through sterilization of a region of the skin infected by bacteria using UV light having a sterilization function. According to embodiments of the present disclosure, the light emitting device is easy to carry and can be used in user activity. According to embodiments of the present disclosure, the light emitting device can be used not only for sterilization of bacteria but also for curing other types of diseases.

DETAILED DESCRIPTION OF EMBODIMENTS

Figure 1:
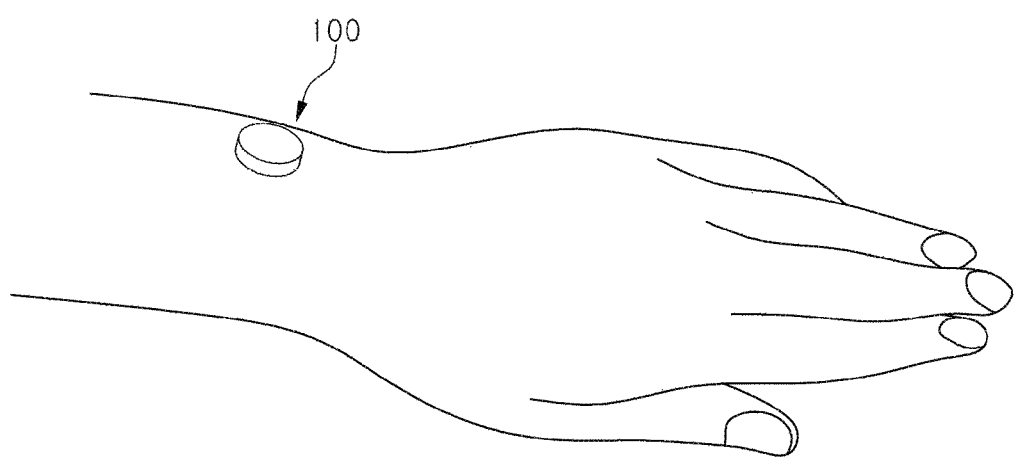
FIG. 1 and FIG. 2 are exemplary views of a light emitting device according to a first embodiment of the present disclosure.

The above and other aspects, features and advantages of the present disclosure will become apparent from the following description of embodiments given in conjunction with the accompanying drawings. The following embodiments are provided by way of example so as to fully convey the spirit of the present disclosure to those skilled in the art to which the present disclosure pertains. Accordingly, the present disclosure is not limited to the embodiments disclosed herein and can also be implemented in different forms. Throughout the accompanying drawings, like elements having the same or similar functions will be denoted by like reference numerals. In addition, although the terms "first", "second", "one surface", "the other surface", "upper surface", "lower surface", "upper portion", "lower portion", and the like are used to distinguish one element or component from other elements or components, these elements or components are not limited by these terms.

Hereinafter, embodiments of the present disclosure will be described in detail with reference to the accompanying drawings.

According to embodiments of the present disclosure, a light emitting device includes: a device housing open at a lower portion thereof; and a sterilization module disposed in the device housing and emitting UV light for sterilization. The sterilization module emits UV light for sterilization toward the open lower portion of the device housing. The sterilization module includes a substrate and at least one light source mounted on one surface of the substrate and emitting the UV light for sterilization. The sterilization module is disposed inside the device housing. The sterilization module may be attached to an upper surface of the device housing.

The light emitting device may further include a transparent member disposed between the sterilization module and the open lower portion of the device housing. The light emitting device may further include a rack protruding from an inner side surface of the device housing and contacting one surface of the substrate.

The rack may be continuously or discontinuously formed along a circumference of the inner side surface of the device housing. In addition, the light source may be disposed between the racks facing each other. The light emitting device may further include a power supply supplying power to the sterilization module.

In one embodiment, the device housing may further include a power supply mount formed on an upper surface thereof and having an opening shape. In addition, power supply is inserted into the power supply mount of the device housing. In another embodiment, the power supply may be disposed between the upper surface of the device housing and the sterilization module.

The sterilization module may include a substrate and a plurality of light sources mounted on one surface of the substrate. At least one of the plurality of light sources emits UV light for sterilization in a different wavelength band from other light sources.

The light emitting device may further include a switch formed on an outer wall of the device housing to select a wavelength band of UV light for sterilization from the light emitting device.

The sterilization module may include a substrate, at least one light source mounted on one surface of the substrate and emitting UV light for sterilization, and a module housing surrounding the substrate and the light source. The module housing may be formed on one surface thereof with a UV light outlet through which the UV light for sterilization passes.

The device housing may be formed of a light transmissive material allowing transmission of the UV light for sterilization therethrough. The sterilization module may be disposed such that the UV light outlet faces an upper surface of the device housing.

In one embodiment, a bonding member may be interposed between one surface of the module housing and the upper surface of the device housing. In another embodiment, the device housing may further include a sterilization module securing portion protruding from the upper surface thereof. The sterilization module securing portion may be bent toward a center of the upper surface of the device housing.

One surface of the module housing may be formed to protrude farther outwards than a side surface thereof. Accordingly, the one surface of the module housing is inserted into the sterilization module securing portion of the device housing such that the sterilization module is secured to the device housing. In another embodiment, the device housing may further include a sterilization module insertion portion formed to pass through an upper surface thereof.

The light emitting device may further include a hanging portion protruding from an inner side surface of the device housing and having elasticity. The sterilization module is inserted into the device housing such that the UV light outlet faces the lower portion of the device housing through the sterilization module insertion portion. In addition, the sterilization module is secured inside the device housing by the hanging portion. Further, the hanging portion may be composed of multiple layers.

The light emitting device may further include a thread formed on an inner wall of the sterilization module insertion portion of the device housing. The light emitting device may further include a thread formed on an outer wall of the module housing. The thread formed on the inner wall of the device housing engages with the thread formed on the outer wall of the module housing to secure the module housing to the device housing. The device housing may be provided on a lower surface thereof with a bonding material.

The light emitting device may further include a band portion bonded at some portion thereof to a lower surface or an outer surface of the device housing and bonded at the other portion thereof to the skin to secure the device housing to the skin. The device housing further includes a bottom portion protruding outwards from a lower surface thereof. The bottom portion is provided on a lower surface thereof with a bonding material.

Here, a band portion is bonded at some portion thereof to an upper surface or a lower surface of the bottom portion and is bonded at the other portion thereof to the skin to secure the device housing to the skin. The light emitting device may further include a sealing member interposed between the bottom portion and the band portion. The light emitting device may further include a reflective member formed on an inner wall or an outer wall of the device housing.

Figure 2:
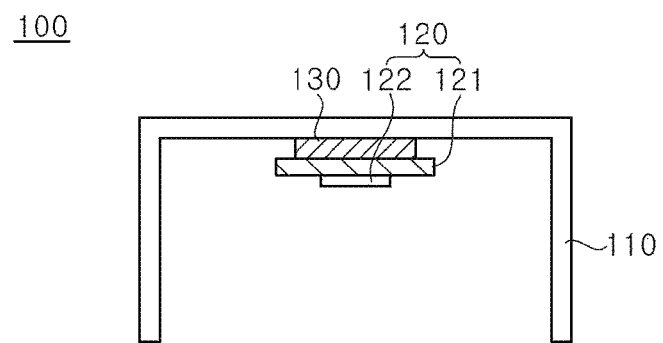

FIG. 1 and FIG. 2 are exemplary views of a light emitting device according to a first embodiment of the present disclosure. A light emitting device 100 according to the present disclosure is a portable light emitting device configured to cure the skin infected by bacteria. Referring to FIG. 1, the light emitting device 100 according to the first embodiment includes a device housing 110, a sterilization module 120, and a power supply 130.

The device housing 110 is formed to have an inner space in which the sterilization module 120 and the power supply 130 are disposed. Further, the device housing 110 is open at a lower portion thereof. That is, an outer portion of the device housing 110 is connected to an inner portion thereof through the lower portion thereof.

The device housing 110 is provided on a lower surface thereof with a bonding material. Accordingly, the device housing 110 is directly bonded to the skin. The device housing 110 may be formed of a material not allowing transmission of UV light for sterilization therethrough. In addition, the device housing 110 may be formed to prevent transmission of UV light for sterilization therethrough and to have transparency so as to ascertain whether the light emitting device 100 is suitably attached to an infected region of the skin.

The sterilization module 120 is disposed inside the device housing 110. In addition, the sterilization module 120 emits UV light for sterilization toward the lower portion of the device housing 110. The sterilization module 120 includes a substrate 121 and a light source 122.

The substrate 121 is electrically connected to the light source 122 and the power supply 130. The substrate 121 receives electric power from the power supply 130 and supplies the electric power to the light source 122.

The light source 122 emits UV light for sterilization. For example, the light source 122 emits UV light in the UVC wavelength band. The light source 122 is disposed on one surface of the substrate 121 to emit the UV light for sterilization through the open lower portion of the device housing 110.

The power supply 130 is disposed on the other surface of the substrate 121. Referring to FIG. 1, one surface of the power supply 130 contacts the other surface of the substrate 121 and the other surface of the power supply 130 contacts an inner upper surface of the device housing 110. That is, the one surface of the power supply 130 is bonded to the substrate 121 and the other surface of the power supply 130 is bonded to the device housing 110 to secure both the power supply 130 and the sterilization module 120 inside the device housing 110. For example, the power supply 130 is a battery.

Antibiotic curing of skin infections caused by bacteria resistant to antibiotics requires a long period of time and entails side effects and high costs. If disease curing takes a long period of time, patients with skin infections also suffer mental stress. The light emitting device 100 provides a different mechanism for skin infections from antibiotic curing as described in detail below.

The light emitting device 100 is attached to the skin through the bonding material disposed on the lower surface of the device housing 110. As shown in FIG. 2, the light emitting device 100 is attached to the skin so as to cover a region of the skin infected by bacteria. The light emitting device 100 attached to the skin emits UV light for sterilization toward the infected region of the skin. In this way, the light emitting device 100 can directly sterilize the infected region of the skin with the UV light for sterilization. Here, a UV blocking material may be applied to normal skin placed in an irradiation range of the UV light for sterilization to protect the normal skin from the UV light for sterilization. The UV blocking material can prevent the occurrence of problems, such as burns, skin cancer, and the like, on the normal skin during sterilization of the infected region. The light emitting device 100 has a small size and is easy to carry. In addition, the light emitting device 100 is formed to cover the infected region of the skin and thus can prevent infiltration of external contaminants into a sterilization region on the skin. As such, the light emitting device 100 has adhesive strength and excellent portability, and can prevent infiltration of external contaminants, thereby enabling sterilization of the infected region during daily life.

In description of a sterilization module according to other embodiments, repeated description of the same components as those of the sterilization module according to previous embodiments will be omitted. For the omitted description, refer to previous description of the sterilization module according to other embodiments.

Figure 3:
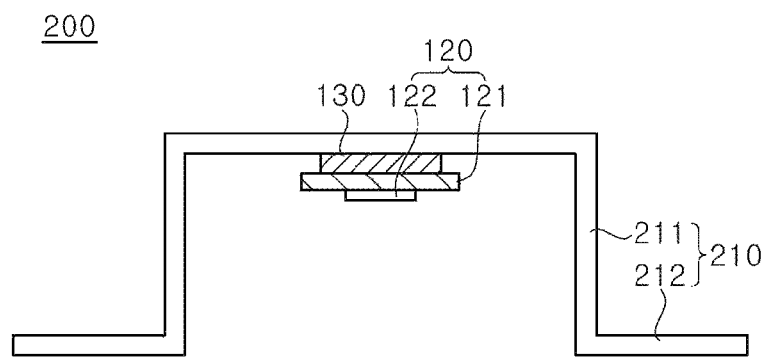
FIG. 3 is an exemplary view of a light emitting device according to a second embodiment of the present disclosure.

FIG. 3 is an exemplary view of a light emitting device according to a second embodiment of the present disclosure. A light emitting device 200 according to the second embodiment includes a device housing 210, a sterilization module 120, and a power supply 130. For the sterilization module 120 and the power supply 130, refer to the description of the light emitting device 100 (see FIG. 1) according to the first embodiment.

The device housing 210 includes a main body 211 and a bottom portion 212. The main body 211 corresponds to a side surface and an upper surface of the device housing 210 and defines an inner surface in which the sterilization module 120 and the power supply 130 are disposed.

The bottom portion 212 protrudes outwards from a lower surface or the side surface of the main body 211. The bottom portion 212 having such a protruding structure is formed along the circumference of the main body 211. In this embodiment, the bottom portion 212 constitutes a lower surface of the device housing 210. The bottom portion 212 is provided on the lower surface thereof with a bonding material.

In some embodiments, the main body 211 and the bottom portion 212 of the device housing 210 are formed as separate components for convenience of description and understanding. In other embodiments, the main body 211 and the bottom portion 212 are integrally formed with each other.

According to this embodiment, the light emitting device 200 includes the bottom portion 212 having a large area and the bonding material is applied to the bottom portion 212, thereby improving bonding strength to the skin. Accordingly, the light emitting device 200 according to this embodiment can be prevented from being separated from the skin during user movement.

Figure 4:
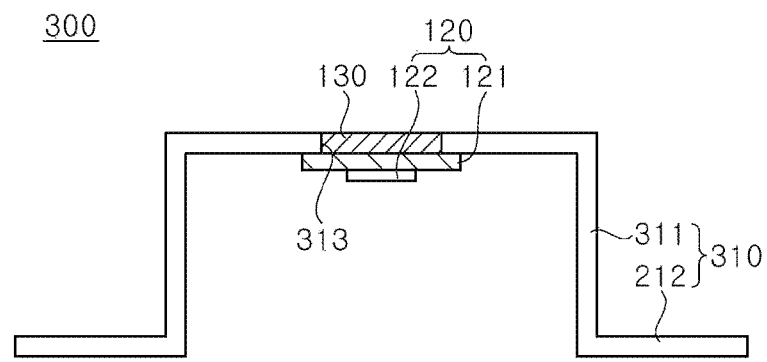
FIG. 4 is an exemplary view of a light emitting device according to a third embodiment of the present disclosure.

FIG. 4 is an exemplary view of a light emitting device according to a third embodiment of the present disclosure. A light emitting device 300 according to the third embodiment includes a device housing 310, a sterilization module 120, and a power supply 130. The device housing 310 includes a main body 311 and a bottom portion 212. The main body 311 is formed on an upper surface thereof with a power supply mount 313 having a through-hole structure. The power supply mount 313 is a space in which the power supply 130 is mounted.

The sterilization module 120 is secured to an inner upper surface of the device housing 310. A light source 122 is secured to one surface of the substrate 121 and the other surface of the substrate 121 is secured to the inner upper surface of the device housing 310. For example, the other surface of the substrate 121 is bonded to the inner upper surface of the device housing 310 via a bonding material. As the other surface of the substrate 121 is bonded to the inner upper surface of the device housing 310, the sterilization module 120 can be secured to the device housing 310.

When the power supply 130 is mounted on the power supply mount 313, the power supply 130 contacts the other surface of the substrate 121 and is electrically connected thereto. In addition, when the power supply 130 is removed from the power supply mount 313, the power supply 130 is electrically disconnected from the substrate 121.

According to this embodiment, the sterilization module 120 may emit UV light for sterilization or may stop emission of the UV light for sterilization by mounting the power supply 130 on the power supply mount 313 or by removing the power supply 130 from the power supply mount 313.

The light emitting device 300 according to this embodiment may adjust a period of time, for which the skin is irradiated with the UV light for sterilization, by mounting or removing the power supply 130. Accordingly, the light emitting device 300 can prevent the skin from being burnt by the UV light for sterilization through regulation of the period of time for which the skin is irradiated with UV light for sterilization.

Figure 5:
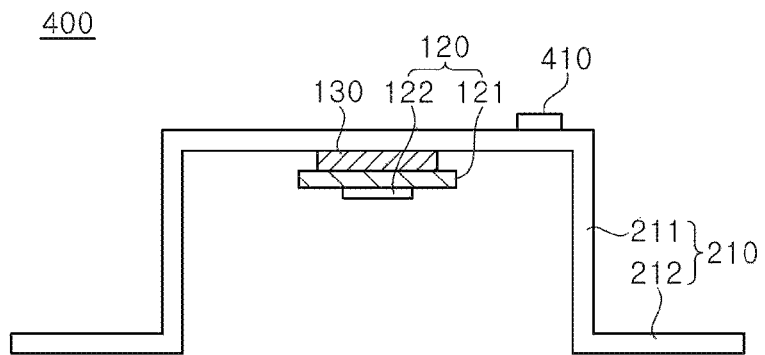
FIG. 5 is an exemplary view of a light emitting device according to a fourth embodiment of the present disclosure.

FIG. 5 is an exemplary view of a light emitting device according to a fourth embodiment of the present disclosure. A light emitting device 400 according to the fourth embodiment includes a device housing 210, a sterilization module 120, and a power supply 130.

The device housing 210 is formed with a power switch 410. Although the power switch 410 is formed on an upper surface of the device housing 210 in FIG. 5, the power switch 410 may be formed in other regions thereof. The power switch 410 serves to ensure that the electric power stored in the power supply 130 is supplied to the sterilization module 120. In addition, the power switch 410 serves to stop the electric power supply to the sterilization module 120.

Therefore, the light emitting device 400 according to this embodiment does not require mounting or removal of the power supply 130 to supply electric power to the sterilization module 120 or to stop power supply thereto. The light emitting device 400 may conveniently perform or stop irradiation of the skin with UV light for sterilization using the power switch 410.

Figure 6:
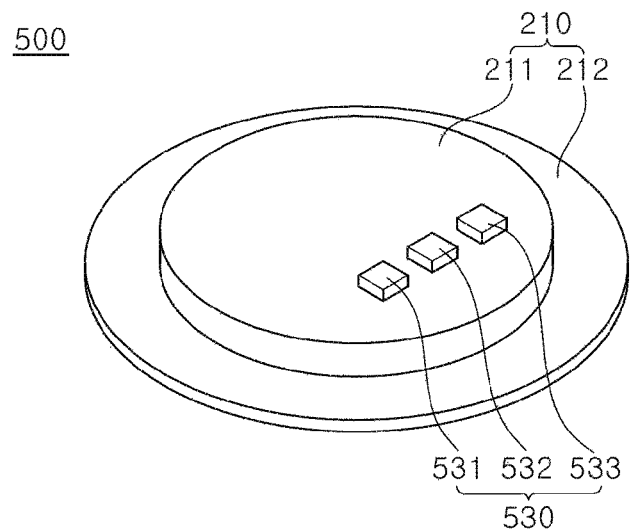
FIG. 6 and FIG. 7 are exemplary views of a light emitting device according to a fifth embodiment of the present disclosure.
Figure 7:
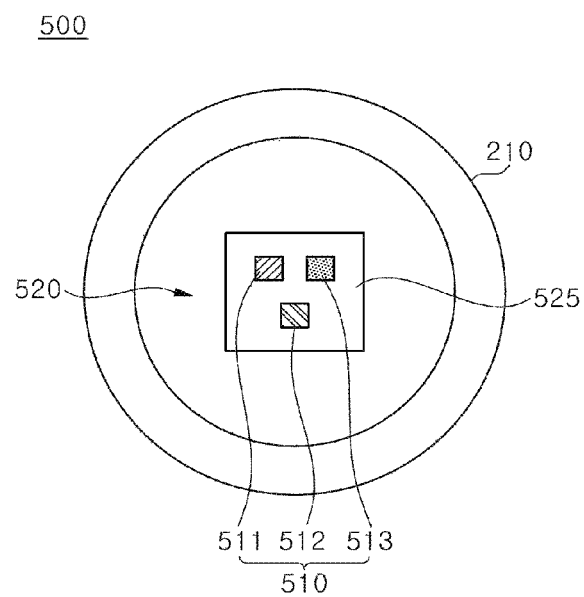

FIG. 6 and FIG. 7 are exemplary views of a light emitting device according to a fifth embodiment of the present disclosure. FIG. 6 is an upper perspective view of a light emitting device 500 and FIG. 7 is a bottom view of the light emitting device 500. The light emitting device 500 according to the fifth embodiment includes a device housing 210 and a sterilization module 520.

The sterilization module 520 includes a substrate 525 and a plurality of light sources 510. The light sources 510 emit UV light in different wavelength bands. For example, the light sources 510 may include a first light source 511, a second light source 512, and a third light source 513. The first light source 511 may emit UV light in the UVC wavelength band. The second light source 512 may emit UV light in the UVB wavelength band. The third light source 513 may emit UV light in the UVA wavelength band. The first to third light sources 511 to 513 are used for other purposes. For example, the first light source 511 may be used for sterilization of bacteria. The second light source 512 may be used to cure atopy, vitiligo, psoriasis, and the like. The third light source 513 may be used to cure atopy, scleroderma, mycosis, and the like.

The device housing 210 is provided with an input switch 530. For example, the input switch 530 includes a first input switch 531, a second input switch 532, and a third input switch 533. The first input switch 531 is connected to the first light source 511. The first input switch 531 allows the first light source 511 to emit UV light or to stop emission of UV light. The second input switch 532 is connected to the second light source 512. The second input switch 532 allows the second light source 512 to emit UV light or to stop emission of UV light. The third input switch 533 is connected to the third light source 513. The third input switch 533 allows the third light source 513 to emit UV light or to stop emission of UV light.

The light emitting device 500 according to this embodiment may emit UV light in a desired wavelength band through the input switch 530 of the device housing 210. Accordingly, the light emitting device 500 according to this embodiment may be used not only for sterilization of bacteria but also other types of skin curing.

Figure 8:
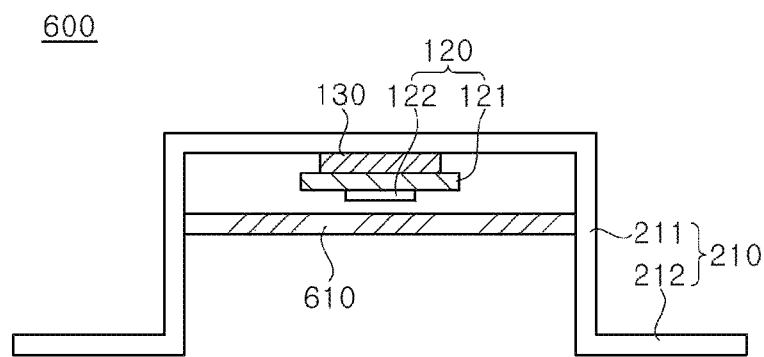
FIG. 8 is an exemplary view of a light emitting device according to a sixth embodiment of the present disclosure.

FIG. 8 is an exemplary view of a light emitting device according to a sixth embodiment of the present disclosure. A light emitting device 600 according to the sixth embodiment includes a device housing 210, a sterilization module 120, a power supply 130, and a transparent member 610. The transparent member 610 is secured inside the device housing 210. In addition, the transparent member 610 is disposed between the sterilization module 120 and a lower surface of the device housing 210.

The transparent member 610 is formed of a material allowing transmission of UV light for sterilization emitted from the sterilization module 120 therethrough. The transparent member 610 shields an installation space of the sterilization module 120 from the outside of the device housing 210. Accordingly, the transparent member 610 protects the sterilization module 120 from external foreign matter, such as dust and moisture.

The transparent member 610 may refract UV light for sterilization. Although the transparent member 610 is illustrated as having a flat structure in FIG. 8, one surface or both surfaces of the transparent member 610 may have a concave shape, a convex shape, or different shapes. In this way, the transparent member 610 may be formed in various shapes to allow UV light for sterilization having passed through the transparent member 610 to be concentrated on a certain region or to be distributed over a broad region.

Figure 9:
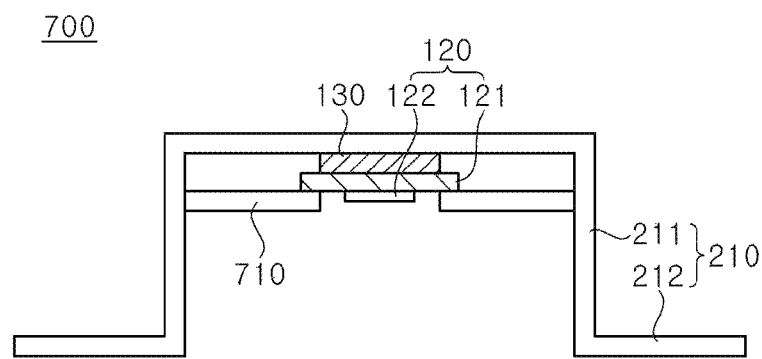
FIG. 9 is an exemplary view of a light emitting device according to a seventh embodiment of the present disclosure.

FIG. 9 is an exemplary view of a light emitting device according to a seventh embodiment of the present disclosure. A light emitting device 700 according to the seventh embodiment includes a device housing 210, a sterilization module 120, a power supply 130, and racks 710. The racks 710 are secured inside the device housing 210. The racks 710 are formed to protrude from an inner side surface of the device housing 210. The racks 710 may be continuously or discontinuously formed along the circumference of the inner side surface of the device housing 210. An empty space may be formed between the racks 710 facing each other.

The sterilization module 120 is placed on the racks 710. One surface of the substrate 121 connected to at least two ends thereof is placed on one surface of the rack 710. In this way, the sterilization module 120 is disposed inside the device housing 210 by the racks 710. When the sterilization module 120 is placed on the racks 710, the light source 122 is disposed between the racks.

Figure 10:
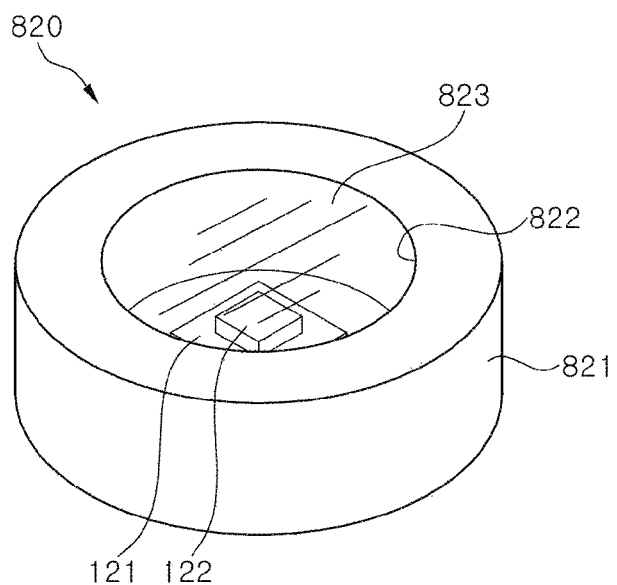
FIG. 10 to FIG. 12 are exemplary views of a light emitting device according to an eighth embodiment of the present disclosure.
Figure 11:
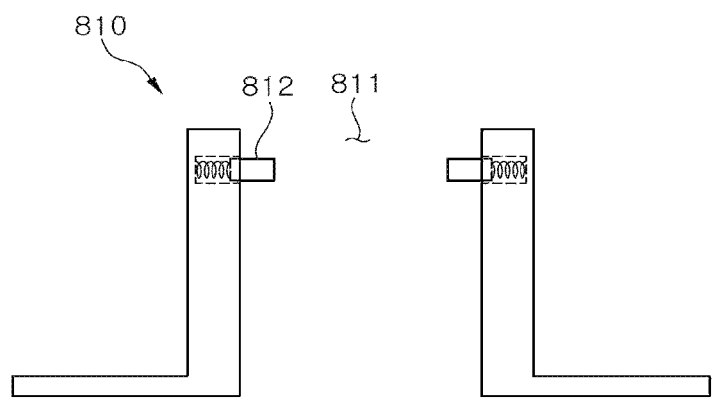
Figure 12:
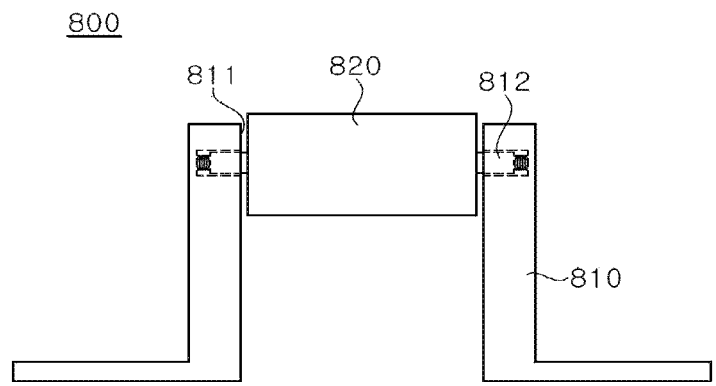

FIG. 10 to FIG. 12 are exemplary views of a light emitting device according to an eighth embodiment of the present disclosure. A light emitting device 800 according to the eighth embodiment includes a device housing 810 and a sterilization module 820. Referring to FIG. 10, the sterilization module 820 includes a module housing 821, a substrate 121, and a light source 122.

The module housing 821 has an inner space defined by at least an upper surface and side surfaces. The substrate 121 and the light source 122 are disposed in the inner space of the module housing 821. Further, the module housing 821 is formed on an upper surface thereof with a UV light outlet 822 having a through-hole structure. The UV light outlet 822 is a path through which UV light for sterilization emitted from the light source 122 is discharged outside the module housing 821.

The substrate 121 and the light source 122 are disposed inside the module housing 821. Further, the substrate 121 is secured inside the module housing 821 and the light source 122 is disposed to face the UV light outlet 822.

The substrate 121 and the light source 122 may be secured inside the module housing 821 by any well-known method using a bonding material, screws, and the like.

The sterilization module 820 may further include a transparent window 823 formed to cover the UV light outlet 822 of the module housing 821. The transparent window 823 may protect the substrate 121 and the light source 122 from foreign matter, such as dust, moisture, and the like, by blocking the interior of the module housing 821 from the exterior of the module housing. In addition, a power supply (now shown) may be disposed inside the sterilization module 820.

Referring to FIG. 11, the device housing 810 includes a sterilization module insertion portion 811 and a hanging portion 812. The sterilization module insertion portion 811 has a through-hole structure penetrating an upper surface of the device housing 810. Through the sterilization module insertion portion 811, at least a portion of the sterilization module 820 is inserted into the device housing 810.

The hanging portion 812 secures the sterilization module 820 to the device housing 810 in a state where the sterilization module 820 is inserted into the device housing 810. The hanging portion 812 protrudes from an inner side surface of the device housing 810. In addition, the hanging portion 812 may be continuously or discontinuously formed along the circumference of the inner side surface of the device housing 810.

The hanging portion 812 is formed to have elasticity. For example, the hanging portion 812 may be bonded at one end thereof to an elastic component, such as a spring, and may be partially inserted into a structure formed on a side surface of the device housing 810, as shown in FIG. 11 to FIG. 12. In this case, the hanging portion 812 is forced to be at least partially inserted into the side surface of the device housing 810. In addition, when the force applied to the hanging portion 812 is removed, the hanging portion 812 is pushed into the interior space of the device housing 810 by the elastic component connected to one end of the hanging portion 812, as shown in FIG. 11. Alternatively, the hanging portion 812 in its entirety may be formed of an elastic material. Various and different designs and configurations are available for the hanging portion 812.

When the sterilization module 820 is inserted into the device housing 810, the hanging portion 812 is pushed toward the inner side surface of the device housing 810 and then presses the sterilization module 820 by elastic force, as shown in FIG. 12. Accordingly, the sterilization module 820 is secured in a state of being inserted into the device housing 810 by the hanging portion 812, as shown in FIG. 12. Here, the sterilization module 820 is inserted into the device housing 810 such that the upper surface of the sterilization module 820 having the UV light outlet 822 formed thereon is directed toward the lower portion of the device housing 810. Thus, UV light for sterilization emitted through the UV light outlet 822 of the sterilization module 820 is discharged through the open lower portion of the device housing 810 and reaches the skin.

In the light emitting device 800 according to this embodiment, the sterilization module 820 is detachably coupled to the device housing 810. When there is a malfunction in the sterilization module 820 integrally formed with the device housing 810, the light emitting device 800 must be replaced. However, since the light emitting device 800 according to this embodiment allows the sterilization module 820 to be detachably coupled to the device housing 810, the light emitting device 800 can be used by replacing the sterilization module 820 with a normal sterilization module.

Figure 13:
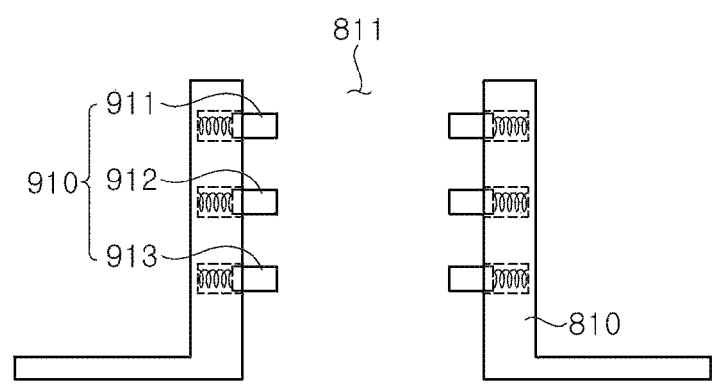
FIG. 13 and FIG. 14 are exemplary views of a light emitting device according to a ninth embodiment of the present disclosure.
Figure 14:
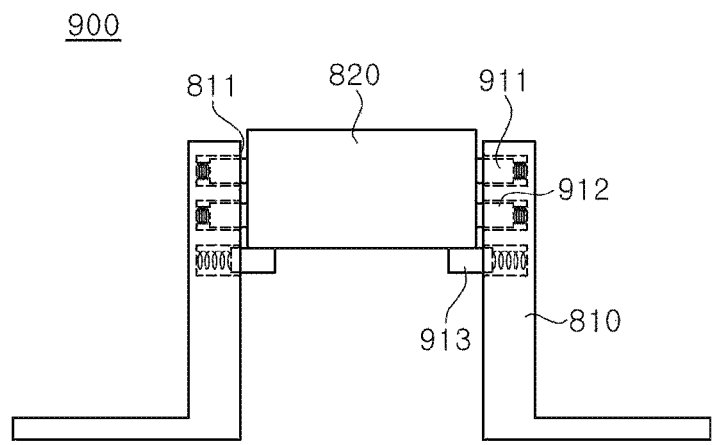

FIG. 13 and FIG. 14 are exemplary views of a light emitting device according to a ninth embodiment of the present disclosure. A light emitting device 900 includes a device housing 810 and a sterilization module 820. Referring to FIG. 13, the device housing 810 includes a sterilization module insertion portion 811 and a hanging portion 910. The sterilization module insertion portion 811 is formed on an upper surface of the device housing 810 and has a penetration structure.

The hanging portion 910 protrudes from an inner side surface of the device housing 810. In addition, the hanging portion 910 is formed to have elasticity. The hanging portion 910 may have the same structure as the hanging portion 812 of the light emitting device 800 (see FIG. 11 and FIG. 12) according to the eighth embodiment.

According to this embodiment, the hanging portion 910 is composed of a plurality of layers. Referring to FIG. 13, the hanging portion 910 is composed of three layers. For convenience of description, the hanging portion 910 includes a first hanging portion 911, a second hanging portion 912, and a third hanging portion 913. The number of layers constituting the hanging portion 910 may be changed, as needed.

Referring to FIG. 14, the sterilization module 820 is inserted into the device housing 810 through the sterilization module insertion portion 811. Here, the sterilization module 820 may be inserted into the device housing 810 to reach a preset location therein. Referring to FIG. 14, the sterilization module 820 is inserted into the device housing 810 such that an upper surface of the sterilization module 820 contacts an upper surface of the first hanging portion 911.

The second hanging portion 912 and the third hanging portion 913 presses the sterilization module 820 to secure the sterilization module 820 inside the device housing 810. In addition, the first hanging portion 911 acts as a buttress preventing the sterilization module 820 from moving downwards.

Such a light emitting device 900 can adjust a securing location of the sterilization module 820 in the device housing 810 through the hanging portion 910 composed of a plurality of layers. That is, the light emitting device 900 can adjust a distance between UV light for sterilization and the skin.

In some embodiments, a region irradiated with UV light for sterilization increases as a distance between the skin and the sterilization module 820 increases. In addition, the region irradiated with UV light for sterilization decreases as the distance between the skin and the sterilization module 820 decreases. Accordingly, the light emitting device 900 allows the entirety of an infected region of the skin to be irradiated with the UV light for sterilization by adjusting the distance between the sterilization module 820 and the skin. Further, the light emitting device 900 may emit UV light for sterilization mainly toward the infected region of the skin by adjusting the distance between the sterilization module 820 and the skin. Here, a UV blocking material may be applied to normal skin placed within an irradiation range of UV light for sterilization to protect the normal skin from the UV light for sterilization. In addition, the light emitting device 900 may prevent the normal skin from being irradiated with UV light for sterilization while allowing the UV light for sterilization to reach only the infected region of the skin by adjusting the distance between the sterilization module 820 and the skin. Here, when only the infected region of the skin is irradiated with the UV light for sterilization, applying the UV blocking material to the normal skin may be avoided.

Figure 15:
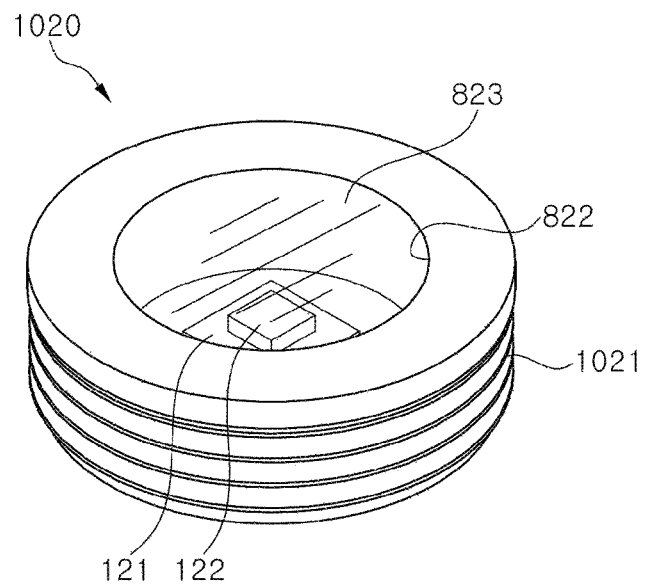
FIG. 15 to FIG. 17 are exemplary views of a light emitting device according to a tenth embodiment of the present disclosure.
Figure 16:
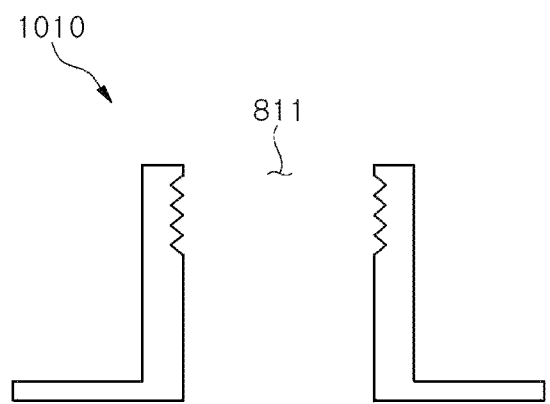
Figure 17:
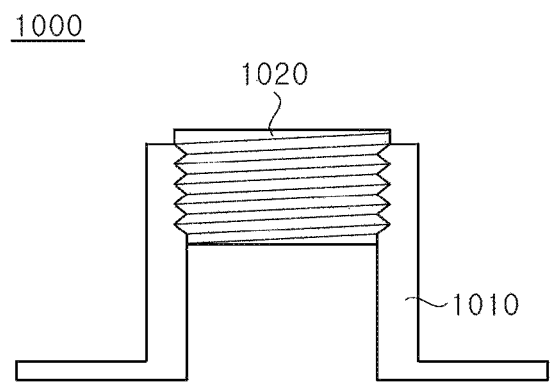

FIG. 15 to FIG. 17 are exemplary views of a light emitting device according to a tenth embodiment of the present disclosure. A light emitting device 1000 according to the tenth embodiment includes a device housing 1010 and a sterilization module 1020.

Referring to FIG. 15, the sterilization module 1020 includes a module housing 1021, a substrate 121, and a light source 122. The substrate 121 and the light source 122 are disposed inside the module housing 1021. The module housing 1021 has a thread formed on an outer surface thereof, as shown in FIG. 15.

Referring to FIG. 16, the device housing 1010 is formed with a sterilization module insertion portion 811. The sterilization module insertion portion 811 has a through-hole structure penetrating an upper surface of the device housing 1010. In addition, a thread is formed on an inner surface of the sterilization module insertion portion 811.

Referring to FIG. 17, the sterilization module 1020 is inserted into the device housing 1010 through the sterilization module insertion portion 811. Here, the outer surface of the module housing 1021 engages with the inner surface of the device housing 1010.

In the light emitting device 1000, the sterilization module 1020 is coupled to the device housing 1010 through screwed type coupling and is secured in a state of being inserted into the device housing 1010.

In addition, since the sterilization module 1020 is coupled to the device housing 1010 through screwed type coupling, the light emitting device 1000 can adjust the securing location of the sterilization module 1020. That is, the light emitting device 1000 can adjust the distance between the sterilization module 1020 and the skin.

A region irradiated with UV light for sterilization increases as a distance between the skin and the sterilization module 1020 increases and the region decreases as the distance between the skin and the sterilization module 1020 decreases. Accordingly, the light emitting device 1000 can adjust a region to be irradiated with the UV light for sterilization through adjustment of a coupling depth of the sterilization module 1020 to the device housing 1010. For example, the light emitting device 1000 allows the entirety of the infected region of the skin to be irradiated with UV light for sterilization by adjusting the coupling depth of the sterilization module 1020 to the device housing 1010. In addition, the light emitting device 1000 may emit UV light for sterilization mainly toward the infected region of the skin by adjusting the distance between the sterilization module 1020 and the skin. Here, a UV blocking material may be applied to normal skin placed within an irradiation range of UV light for sterilization to protect the normal skin from the UV light for sterilization. In addition, the light emitting device 1000 may prevent the normal skin from being irradiated with UV light for sterilization while allowing the UV light for sterilization to reach only the infected region of the skin by adjusting the distance between the sterilization module 1020 and the skin. Here, when only the infected region of the skin is irradiated with the UV light for sterilization, it is not necessary to apply the UV blocking material to the normal skin.

Figure 18:
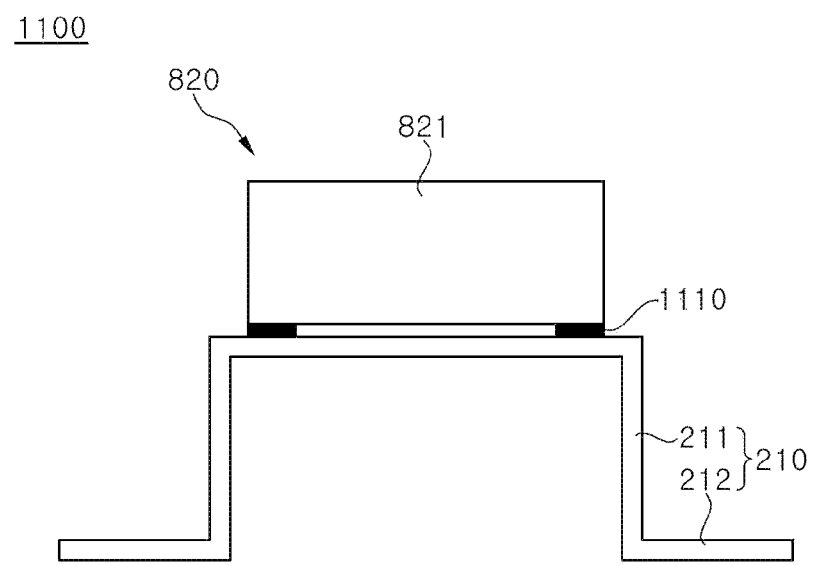
FIG. 18 is an exemplary view of a light emitting device according to an eleventh embodiment of the present disclosure.

FIG. 18 is an exemplary view of a light emitting device according to an eleventh embodiment of the present disclosure. A light emitting device 1100 according to the eleventh embodiment includes a device housing 210, a sterilization module 820, and a bonding member 1110. The device housing 210 is formed of a material allowing transmission of UV light for sterilization therethrough.

Although the sterilization module 820 is not shown, the substrate and the light source are disposed inside the module housing 821. Further, the module housing 821 is formed on an upper surface thereof with a UV light outlet (not shown) having a through-hole structure. The substrate and the light source are disposed inside the module housing 821 such that UV light for sterilization is directed toward the UV light outlet.

The sterilization module 820 is disposed on the device housing 210. Here, the sterilization module 820 is disposed on the device housing 210 such that the UV light outlet of the module housing 821 faces the upper surface of the device housing 210. Accordingly, UV light for sterilization emitted from the sterilization module 820 reaches the skin through the upper surface of the device housing 210.

The bonding member 1110 is formed between the sterilization module 820 and the device housing 210. The bonding member 1110 improves bonding strength between the sterilization module 820 and the device housing 210 to prevent the sterilization module 820 from being separated from the device housing 210.

Figure 19:
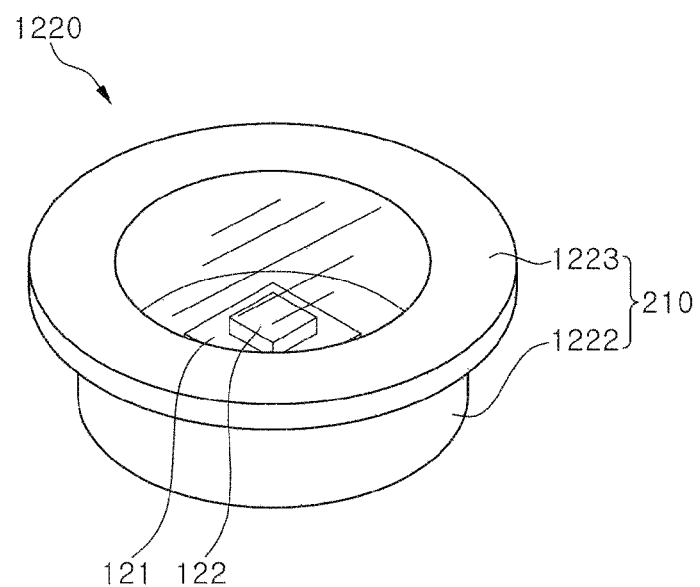
FIG. 19 to FIG. 21 are exemplary views of a light emitting device according to a twelfth embodiment of the present disclosure.
Figure 20:
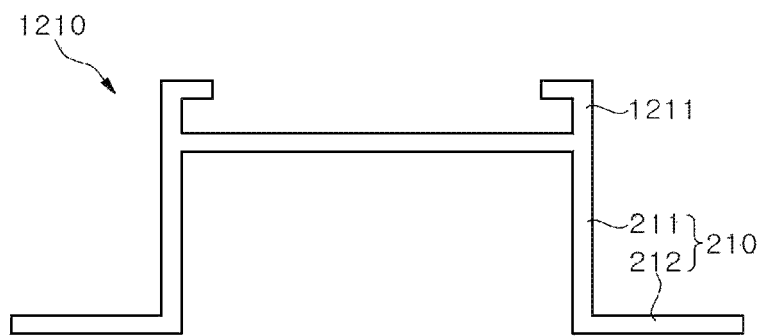
Figure 21:
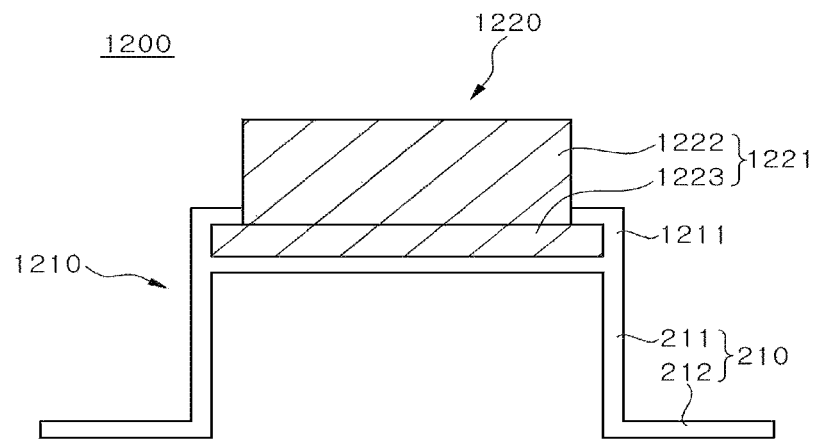

FIG. 19 to FIG. 21 are exemplary views of a light emitting device according to a twelfth embodiment of the present disclosure. A light emitting device 1200 according to the twelfth embodiment includes a device housing 1210 and a sterilization module 1220.

Referring to FIG. 19, the device housing 1210 is formed of a material allowing transmission of UV light for sterilization therethrough. In addition, the device housing 1210 is formed on an upper surface thereof with a sterilization module securing portion 1211. The sterilization module securing portion 1211 is formed to protrude from the upper surface of the device housing 1210. In addition, the sterilization module securing portion 1211 is formed to be bent toward the center of the upper surface of the device housing 1210.

The sterilization module securing portion 1211 may be continuously or discontinuously formed along the circumference of the upper surface of the device housing 1210. In addition, the sterilization module securing portion 1211 may be formed to have elasticity.

Referring to FIG. 20, the sterilization module 1220 includes a module housing 1221, a substrate 121, and a light source 122. The substrate 121 and the light source 122 are disposed inside the sterilization module 1220.

The module housing 1221 includes a lateral portion 1222 and an upper surface portion 1223. The upper surface portion 1223 is formed to cover an upper surface of the lateral portion 1222 and to protrude outwards from the lateral portion 1222. In addition, the sterilization module 1220 emits UV light for sterilization outwards through the upper surface portion 1223.

Referring to FIG. 21, the sterilization module 1220 is disposed on an upper surface of the device housing 1210. Here, the upper surface portion 1223 of the module housing 1221 is inserted into the sterilization module securing portion 1211 of the device housing 1210. Since the sterilization module securing portion 1211 is formed to have elasticity, the upper surface portion 1223 of the module housing 1221 can be easily inserted.

As such, the light emitting device 1200 can secure the sterilization module 1220 to the device housing 1210 by fitting the upper surface portion 1223 of the module housing 1221 into the sterilization module securing portion 1211 of the device housing 1210.

Figure 22:
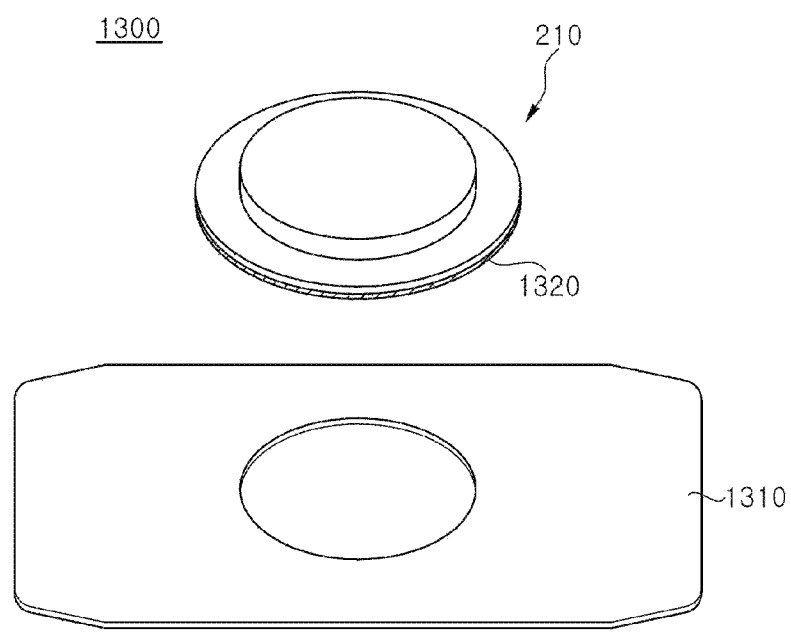
FIG. 22 and FIG. 23 are exemplary views of a light emitting device according to a thirteenth embodiment of the present disclosure.
Figure 23:
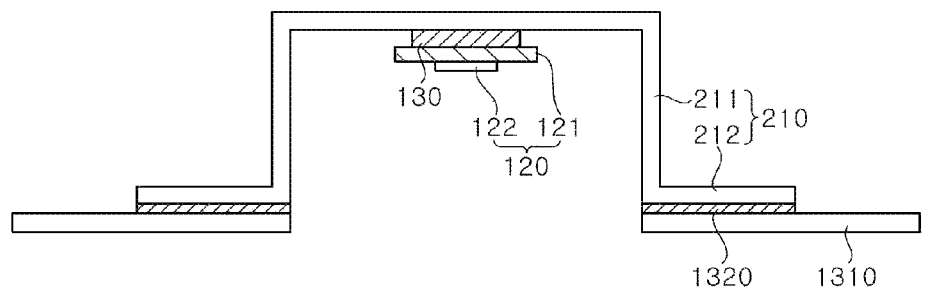

FIG. 22 and FIG. 23 are exemplary views of a light emitting device according to a thirteenth embodiment of the present disclosure. A light emitting device 1300 according to the thirteenth embodiment includes a device housing 210, a sterilization module 120, a bonding member 1320, and a band portion 1310.

The band portion 1310 is provided on a lower surface thereof with a bonding material, by which the band portion 1310 is brought into close contact with the skin. In addition, the band portion 1310 is formed of a flexible material. Accordingly, the band portion 1310 can be maintained in a close contact state with the skin even when the band portion is bonded to a curved region of the skin or when the skin is moved.

In this embodiment, the device housing 210 is disposed on an upper surface of the band portion 1310. In addition, the bonding member 1320 is formed between the device housing 210 and the band portion 1310. The device housing 210 is bonded and secured to the band portion 1310 by the bonding member 1320. The bonding member 1320 may be provided as an independent component with respect to the device housing 210 and the band portion 1310, or may be provided in the form of being previously attached to the lower surface of the device housing 210.

Since the band portion 1310 is flexibly attached to the skin, the light emitting device 1300 according to this embodiment can be easily attached to a curved region of the skin and can maintain an attached state even when the attached region of the skin is moved.

The device housing 210 is secured to the skin. In addition, the band portion 1310 is formed of a flexible material capable of being brought into close contact with the skin.

In addition, the light emitting device 1300 allows individual separation of the band portion 1310 and the device housing 210 in which the sterilization module 120 is disposed. Accordingly, when there is a malfunction in the sterilization module 120 or the device housing 210, it is possible to replace the sterilization module 120 and the device housing 210 while allowing the band portion 1310 to be maintained in a state of being attached to the skin. That is, the sterilization module 120 enables replacement of a defective component only, thereby reducing repair costs.

Figure 24:
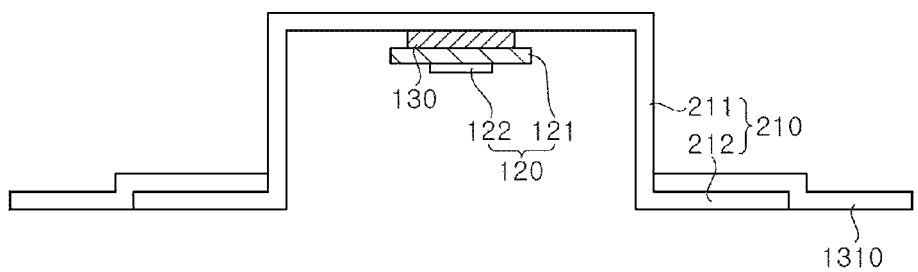
FIG. 24 is an exemplary view of a light emitting device according to a fourteenth embodiment of the present disclosure.

FIG. 24 is an exemplary view of a light emitting device according to a fourteenth embodiment of the present disclosure. A light emitting device 1400 according to the fourteenth embodiment includes a device housing 210, a sterilization module 120, and a band portion 1310. The sterilization module 120 is disposed inside the device housing 210 to emit UV light for sterilization toward a lower portion of the device housing 210.

The band portion 1310 is disposed on an upper surface of a bottom portion 212 of the device housing 210. The band portion 1310 is provided on a lower surface thereof with a bonding material. Accordingly, the band portion 1310 is bonded to the device housing 210 without a separate bonding member. In addition, the band portion 1310 is formed of a flexible material.

As shown in FIG. 24, in the light emitting device 1400, the band portion 1310 is bonded to the skin while covering the bottom portion 212 of the device housing 210. Accordingly, the device housing 210 of the light emitting device 1400 may be tightly secured to the skin by the band portion 1310 without a separate bonding material on the lower surface of the bottom portion 212.

Figure 25:
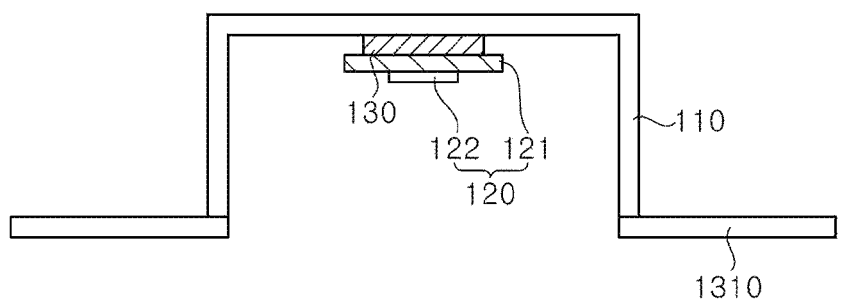
FIG. 25 is an exemplary view of a light emitting device according to a fifteenth embodiment of the present disclosure.

FIG. 25 is an exemplary view of a light emitting device according to a fifteenth embodiment of the present disclosure. A light emitting device 1500 according to the fifteenth embodiment includes a device housing 110, a sterilization module 120, and a band portion 1310. The sterilization module 120 is disposed inside the device housing 110 to emit UV light for sterilization toward the lower portion of the device housing 110.

The device housing 110 is not formed with a bottom portion, like the device housing 110 (see FIG. 2). The band portion 1310 is bonded to a lower surface of the device housing 110. Although not shown in the drawings, the band portion 1310 is bonded to the lower surface of the device housing 110 via a bonding material.

In the light emitting device 1500, the lower surface of the device housing 110 to be secured to the skin is hard and has a small area. Since the hard lower surface of the device housing 110 has a small width, it is possible to suppress widening of a gap between the lower surface of the device housing 110 and the skin due to movement of the skin. Even when the gap between the lower surface of the device housing 110 and the skin is widened, a fraction of the band portion 1310 separated from the skin by the device housing 110 is limited due to the small width of the lower surface of the device housing 110. Accordingly, the light emitting device 1500 according to this embodiment is suitable for a region of the skin having frequent motions.

Figure 26:
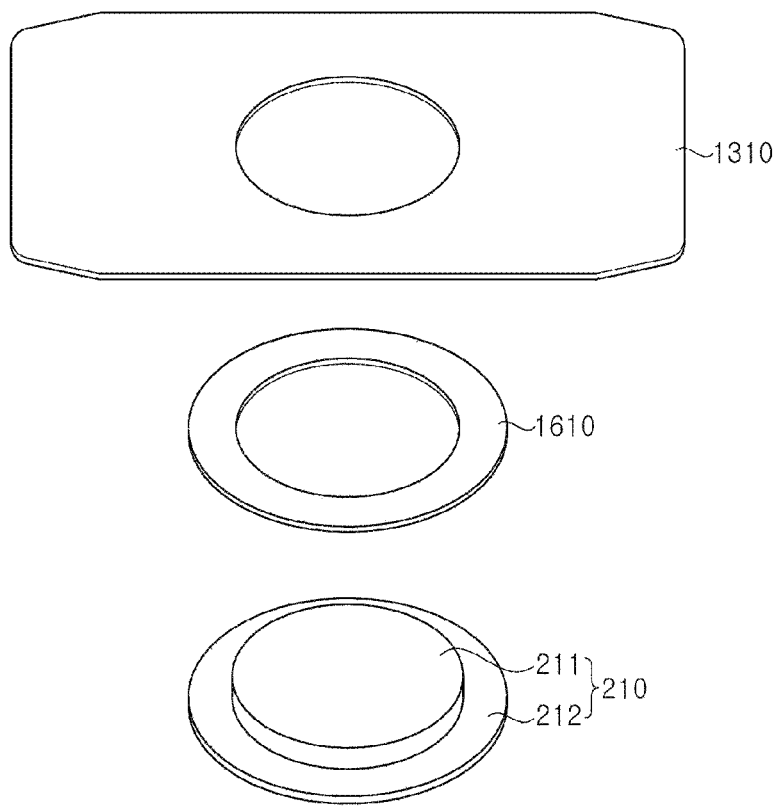
FIG. 26 and FIG. 27 are exemplary views of a light emitting device according to a sixteenth embodiment of the present disclosure.
Figure 27:
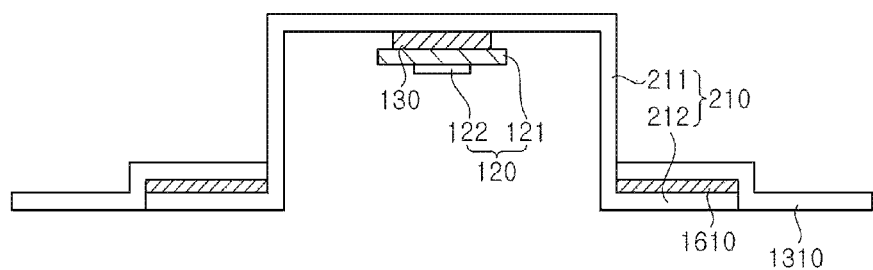

FIG. 26 and FIG. 27 are exemplary views of a light emitting device according to a sixteenth embodiment of the present disclosure. A light emitting device 1600 according to the sixteenth embodiment includes a device housing 210, a sterilization module 120, a band portion 1310, and a sealing member 1610. The sterilization module 120 is disposed inside the device housing 210.

The band portion 1310 is bonded to the skin while covering an upper side of a bottom portion 212 of the device housing 210. The sealing member 1610 is disposed between the band portion 1310 and the bottom portion 212 of the device housing 210. The sealing member 1610 may be formed of a material such as sponge, silicone, and the like. The sealing member 1610 seals a gap between the band portion 1310 and the bottom portion 212 of the device housing 210. Accordingly, the sealing member 1610 prevents moisture from entering the light emitting device 1600. The light emitting device 1600 according to the present disclosure has improved waterproofing by the sealing member 1610.

Figure 28:
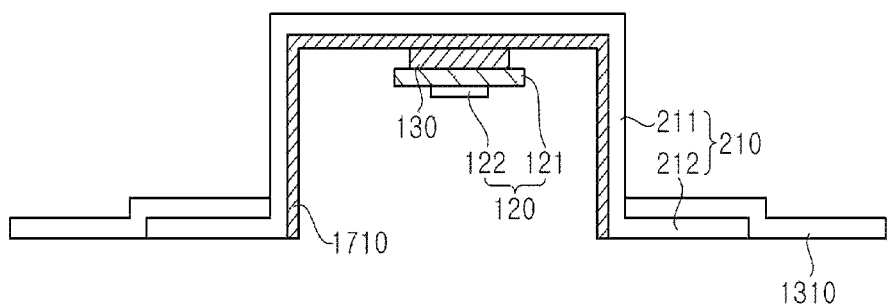
FIG. 28 is an exemplary view of a light emitting device according to a seventeenth embodiment of the present disclosure.

FIG. 28 is an exemplary view of a light emitting device according to a seventeenth embodiment of the present disclosure. A light emitting device 1700 includes a device housing 210, a sterilization module 120, and a band portion 1310. The sterilization module 120 is disposed inside the device housing 210. The band portion 1310 is bonded to the skin while covering an upper side of a bottom portion 212 of the device housing 210.

A reflective member 1710 is formed on an inner wall of the device housing 210. For example, the reflective member 1710 may be formed by coating the inner wall of the device housing 210 with a reflective material.

UV light for sterilization emitted from the sterilization module 120 is reflected by the reflective member 1710 upon reaching the inner wall of the device housing 210. The reflective member 1710 can prevent the UV light for sterilization from escaping from the light emitting device 1700. Accordingly, the light emitting device 1700 according to this embodiment has improved luminous efficacy through formation of the reflective member 1710 on the inner wall of the device housing 210, thereby improving sterilization efficiency.

Although the reflective member 1710 is illustrated as being formed on the inner wall of the device housing 210 in this embodiment, it should be understood that the present disclosure is not limited thereto. The reflective member 1710 may be formed not only on the inner wall of the device housing 210 but also on an outer wall thereof. Alternatively, the reflective member 1710 may be formed on the bottom portion 212.

Although some embodiments have been described herein, it should be understood that these embodiments are provided for illustration only and are not to be construed in any way as limiting the present disclosure, and that the scope of the present disclosure should be defined by the appended claims and equivalents thereto.

We claim:

1. A light emitting device comprising:
    a device housing open at a lower portion thereof; and
    a sterilization module disposed in the device housing and emitting light for sterilization toward the open lower portion of the device housing, the sterilization module comprising:
    a substrate;

at least one light source mounted on one surface of the substrate and emitting the light for sterilization; and a module housing surrounding the substrate and the light source, wherein the module housing is formed on one surface thereof with a light outlet through which the light for sterilization passes, wherein the device housing is formed of a light transmissive material allowing transmission of the UV light for sterilization therethrough.

2. The light emitting device according to claim 1, further comprising:

a power supply supplying power to the sterilization module.

3. The light emitting device according to claim 1, wherein the sterilization module comprises a plurality of light sources and at least one of the light sources emits light for sterilization in a different wavelength band from other light sources.

4. The light emitting device according to claim 3, further comprising:

a switch formed on an outer wall of the device housing and selecting a wavelength band of light for sterilization from the light emitting device.

5. The light emitting device according to claim 1, wherein the sterilization module is disposed such that the light outlet faces an upper surface of the device housing.

6. The light emitting device according to claim 5, wherein a bonding member is interposed between one surface of the module housing and the upper surface of the device housing.

7. The light emitting device according to claim 5, wherein the device housing further comprises a sterilization module securing portion protruding from the upper surface thereof, the sterilization module securing portion being bent toward a center of the upper surface of the device housing.

8. The light emitting device according to claim 7, wherein one surface of the module housing is formed to protrude farther outwards than a side surface thereof, the one surface of the module housing being inserted into the sterilization module securing portion of the device housing.

9. The light emitting device according to claim 1, wherein the device housing further comprises a sterilization module insertion portion formed to pass through an upper surface thereof.

10. The light emitting device according to claim 9, further comprising:

a hanging portion protruding from an inner side surface of the device housing and having elasticity.

11. The light emitting device according to claim 10, wherein the sterilization module is inserted into the device housing such that the light outlet faces the lower portion of the device housing through the sterilization module insertion portion, the sterilization module being secured inside the device housing with the hanging portion.

12. The light emitting device according to claim 9, further comprising:

a thread formed on an inner wall of the sterilization module insertion portion of the device housing; and a thread formed on an outer wall of the module housing, and wherein the thread formed on the inner wall of the device housing engages with the thread formed on the outer wall of the module housing to secure the module housing to the device housing.

13. The light emitting device according to claim 1, wherein the device housing is provided on a lower surface thereof with a bonding material.

14. The light emitting device according to claim 1, further comprising:

a band portion bonded at some portion thereof to a lower surface or an outer surface of the device housing and bonded at another portion thereof to a skin area to secure the device housing to the skin area.

15. The light emitting device according to claim 1, wherein the device housing further comprises a bottom portion protruding outwards from a lower surface thereof.

16. The light emitting device according to claim 15, wherein the bottom portion is provided on a lower surface thereof with a bonding material.

17. The light emitting device according to claim 15, further comprising:

a band portion bonded at some portion thereof to an upper surface or a lower surface of the bottom portion and bonded at the other portion thereof to a skin area to secure the device housing to the skin area.

18. The light emitting device according to claim 17, further comprising:

a sealing member interposed between the bottom portion and the band portion.

19. The light emitting device according to claim 1, further comprising:

a reflective member formed on an inner wall, an outer wall, or both of the device housing.

* * * * *